United States Patent
Starkebaum

(10) Patent No.: US 7,177,693 B2
(45) Date of Patent: *Feb. 13, 2007

(54) GASTRIC STIMULATION FOR ALTERED PERCEPTION TO TREAT OBESITY

(75) Inventor: Warren L. Starkebaum, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 224 days.

This patent is subject to a terminal disclaimer.

(21) Appl. No.: 10/768,716

(22) Filed: Jan. 30, 2004

(65) Prior Publication Data

US 2005/0149141 A1 Jul. 7, 2005

Related U.S. Application Data

(60) Provisional application No. 60/535,143, filed on Jan. 7, 2004.

(51) Int. Cl.
*A61N 1/18* (2006.01)

(52) U.S. Cl. .......................................... 607/40; 607/133
(58) Field of Classification Search .................. 607/40, 607/133
See application file for complete search history.

(56) References Cited

U.S. PATENT DOCUMENTS

| | | | | |
|---|---|---|---|---|
| 4,535,777 A | * | 8/1985 | Castel | 607/71 |
| 5,188,104 A | * | 2/1993 | Wernicke et al. | 607/40 |
| 5,423,872 A | | 6/1995 | Cigaina | |
| 5,690,691 A | | 11/1997 | Chen et al. | |
| 5,836,994 A | | 11/1998 | Bourgeois | |
| 5,861,014 A | | 1/1999 | Familoni | |
| 5,995,872 A | | 11/1999 | Bourgeois | |
| 6,041,258 A | | 3/2000 | Cigaina et al. | |
| 6,091,992 A | | 7/2000 | Bourgeois et al. | |
| 6,104,955 A | | 8/2000 | Bourgeois | |
| 6,115,635 A | | 9/2000 | Bourgeois | |
| 6,216,039 B1 | | 4/2001 | Bourgeois | |
| 6,327,503 B1 | | 12/2001 | Familoni | |
| 6,542,776 B1 | | 4/2003 | Gordon et al. | |
| 6,606,523 B1 | | 8/2003 | Jenkins | |
| 6,611,715 B1 | * | 8/2003 | Boveja | 607/40 |
| 6,615,084 B1 | | 9/2003 | Cigaina | |
| 6,684,104 B2 | * | 1/2004 | Gordon et al. | 607/40 |
| 6,853,862 B1 | * | 2/2005 | Marchal et al. | 607/40 |
| 2002/0072780 A1 | | 6/2002 | Foley | |
| 2004/0088022 A1 | * | 5/2004 | Chen | 607/40 |

OTHER PUBLICATIONS

Koch, Chapter 13-Electrogastrography, Gastrointestinal Motility in Health and Disease, 2002, p. 198, 2nd Edition.
Lacy, Chapter 10-Manometry, Gastrointestinal Motility in Health and Disease, 2002, p. 1478, 2nd Edition.

* cited by examiner

*Primary Examiner*—Robert E. Pezzuto
*Assistant Examiner*—Tammie K. Heller
(74) *Attorney, Agent, or Firm*—Mary P. Bauman; Medtronic, Inc.

(57) ABSTRACT

In general, an implantable medical device is disclosed for generating and applying an electric stimulation signal to a portion of a patient's gastrointestinal tract to induce symptoms of gastroparesis in the patient without substantially reducing normal stomach motility. The induced symptoms of gastroparesis may reduce a patient's desire to consume large portions of food and thus provide an effective treatment for obesity.

13 Claims, 7 Drawing Sheets

GASTRIC STIMULATION FOR ALTERED PERCEPTION TO TREAT OBESITY

RELATED PATENTS

This application claims the benefit of U.S. Provisional Application to Starkebaum, entitled, "GASTRIC STIMULATION FOR ALTERED PERCEPTION TO TREAT OBESITY," Ser. No. 60/535,143, filed Jan. 7, 2004.

FIELD OF THE INVENTION

The invention relates to medical devices and methods, and in particular, to medical devices and methods for electrical stimulation of the stomach for treatment of obesity.

BACKGROUND

Obesity is a major health concern in the United States as well as other western countries. A significant portion of the population is overweight with the number increasing every year. Obesity is one of the leading causes of preventable death. Obesity is associated with several co-morbidities that affect almost every body system. Some of these co-morbidities include: hypertension, heart disease, stroke, high cholesterol, diabetes, coronary disease, breathing disorders, sleep apnea, cancer, gallstones, and musculoskeletal problems. An obese patient is also at increased risk of developing Type II diabetes.

Multiple factors contribute to obesity, including physical inactivity and overeating. Existing therapies include diet, exercise, appetite suppressive drugs, metabolism enhancing drugs, surgical restriction of the gastric tract, and surgical modification of the gastric tract. These therapies may result in little or no weight loss up to weight loss of nearly 50% of initial body weight.

Natural feedback mechanisms, such as the normal sensation of fullness following a meal, may be insufficient for a patient to regulate his own behavior. In addition, natural feedback mechanisms may be inadequate to control a patient's behavior. An obese patient, for example, may continue to consume food after being full because of a delay between onset of fullness and the onset of the sensation of fullness.

Gastroparesis is an adverse medical condition in which normal gastric motor function is impaired. Gastroparesis is also called delayed gastric emptying as the stomach takes too long to empty its contents. Typically, gastroparesis results from muscles of the stomach and intestines not working normally, and movement of food through the stomach slows or stops. Patients with gastroparesis typically exhibit symptoms of nausea and/or vomiting and gastric discomfort. They may complain of bloating or a premature or extended feeling of fullness (satiety). The symptoms of gastroparesis are the result of reduced gastric motility. Gastroparesis generally results in patients reducing food intake and subsequently losing weight.

Electric stimulation of the gastrointestinal tract has been proposed as a mechanism for treating morbid obesity. Table 1 below lists examples of documents that disclose techniques for electric stimulation of the gastrointestinal tract for the treatment of various conditions including obesity. These disclosures suggest that disruption in the normal stomach motility which may then cause symptoms of gastroparesis may be useful in the treatment of obesity.

Experimental results suggest that electric stimulation of the gastrointestinal tract that results in disruption of normal stomach motility requires simulation pulses approximately equal to a normal human stomach's gastric slow wave of approximately 3 cycles per minute (cpm). A gastric slow wave corresponds to a contraction propagation frequency in a human stomach used to cause movement of contents within the gastrointestinal tract.

TABLE 1

| Pat. No. | Inventors | Title |
|---|---|---|
| 20020072780 | Foley | Method and apparatus for intentional impairment of gastric motility and /or efficiency by triggered electrical stimulation of the gastrointestinal tract with respect to the intrinsic gastric electrical activity |
| 6,327,503 | Familoni | Method and apparatus for sensing and stimulating gastrointestinal tract on-demand |
| 5,836,994 | Bourgeois | Method and apparatus for electrical stimulation of the gastrointestinal tract |
| 5,995,872 | Bourgeois | Method and apparatus for electrical stimulation of the gastrointestinal tract |
| 6,091,992 | Bourgeois | Method and apparatus for electrical stimulation of the gastrointestinal tract |
| 6,104,955 | Bourgeois | Method and apparatus for electrical stimulation of the gastrointestinal tract |
| 6,115,635 | Bourgeois | Method and apparatus for electrical stimulation of the gastrointestinal tract |
| 6,216,039 | Bourgeois | Method and apparatus for treating irregular gastric rhythms |
| 5,423,872 | Cigiana | Process and Device for Treating Obesity and Syndromes Relates to Motor Disorders of the Stomach of a Patient |
| 6,542,776 | Gordon et al. | Gastric Stimulator and Method for Installing |
| 6,606,523 | Jenkins | Gastric Stimulator Apparatus and Method for Installing |
| 6,615,084 | Cigiana | Process for Electrostimulation Treatment of Morbid Obesity |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY

In general, the invention is directed to methods and devices for generating an electric stimulation signal to induce symptoms of gastroparesis. The induced symptoms of gastroparesis may reduce a patient's desire to consume large portions of food and thus provide an effective treatment for obesity. In some embodiments, the electrical stimulation may be selected to induce symptoms of gastroparesis in the patient, yet avoid substantial disruption of actual, normal stomach motility.

The symptoms of gastroparesis suggest that some effects of inducing merely symptoms of gastroparesis, rather than gastroparesis itself, may be beneficial as a therapy for obesity, if the symptoms are properly modulated. More significantly, the symptomology of gastroparesis, if associated with gastric activity, may provide an effective form of therapy for the treatment of obesity.

Various embodiments of the present invention provide solutions to one or more problems existing in the prior art with respect to prior techniques for treatment of obesity. These problems include the limited effectiveness of diet and exercise for some patients, as well as the lack of availability of extensive exercise as a viable option for extremely obese persons. Additional problems relate to the health risks associated with intake of appetite suppressive drugs and metabolism enhancing drugs, as well as the ineffectiveness of such substances for some patients. A further problem is the need for surgical intervention and recovery to accomplish other treatments for obesity, such as surgical restriction or modification of the gastric tract.

As another problem, if electrical stimulation is used to induce gastroparesis to treat obesity, disruption of stomach motility as a result of inducing gastroparesis has significant drawbacks, such as adverse health effects associated with continued disruption of normal stomach motility. While inducing symptoms of gastroparesis may discourage patients from consuming large quantities of food, inducing gastroparesis by disrupting normal stomach motility as a mechanism to induce its symptoms may result in undesired consequences. Patients being treated for obesity continue to use their gastrointestinal tract to maintain their health. Disruption of normal gastrointestinal activities may result in a reduced ability to receive nutrition. As a result, gastric electric stimulation-based treatments for obesity existing in the prior art may result in an undesirable reduction in an ability to receive nutrition while attempting to assist a patient in weight loss.

Various embodiments of the present invention are capable of solving at least one of the foregoing problems. When embodied as an implantable device, for example, the invention includes various features including a processor that generates gastric electric stimulation to the patient with characteristics selected to induce symptoms of gastroparesis without substantially disrupting stomach motility. The processor may operate in response to external commands received from an external module. The processor performs operations indicated by the external commands to determine when gastric electric stimulation is to be initiated and when gastric electric stimulation is to be terminated. Using the external module, a patient may activate electrical stimulation coincident to food intake, avoiding continuous delivery of electrical stimulation.

In comparison to known implementations of gastric stimulation used for the treatment of obesity, various embodiments of the invention may provide one or more advantages. The invention provides gastric electric stimulation induce useful symptoms in the treatment of obesity using an electric stimulation signal possessing characteristics that do not disrupt normal stomach motility. As such, the invention may provide more effective treatment for obesity while providing considerable freedom and enjoyment of life for the patient, and reducing adverse health effects associated with disruption of stomach motility due to inducement of gastroparesis. The gastric electrical stimulation may be delivered by an implanted medical device in response to commands from an external module. In various embodiments, the patient can use the invention to advantageously reduce consumption of food and provide an effective mechanism for exercise control over his or her own health and well-being.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
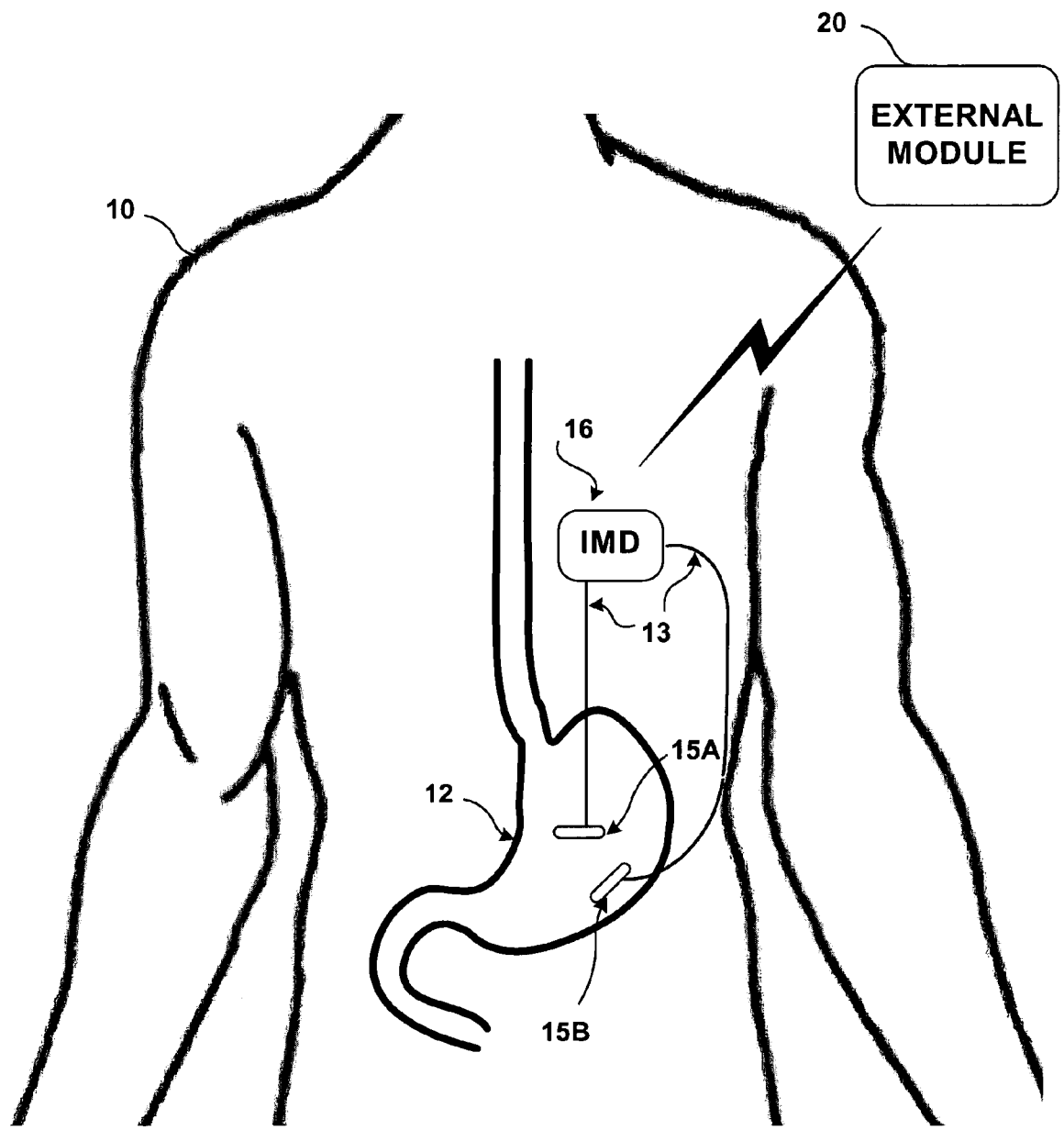
FIGS. 1A and 1B are diagrams illustrating devices for monitoring activity of the stomach and providing electric stimulation to patient responsive to stomach activity.

FIG. 1 is a block diagram illustrating a view of a torso of a patient 10, in which stomach 12 is visible. FIG. 1 further illustrates an implantable medical device 16 for providing electric stimulation to patient 10. In accordance with the invention, the electrical stimulation has one or more characteristics selected to induce symptoms of gastroparesis without substantially disrupting normal stomach motility. In this manner, the patient may experience a feelings of nausea, satiety, bloating or discomfort, yet exhibit substantially normal stomach motility.

IMD 16 may be used to generate electric stimulation of the gastric tract via one or more stimulation electrodes 15A, 15B (hereinafter referred to as "stimulation electrodes 15"). Stimulation electrodes 15A, 15B may be affixed to an external surface of the stomach via sutures, surgical adhesives, or the like. Experimental results have shown that stimulation electrodes 15 may be implanted at many locations within the stomach as it is believed that the electrical stimulation couples to the vagal nerve to transmit signals to a patient's brain. As such, any location in which the electrical coupling to the nerve is possible may be used.

Stimulation electrodes 15A, 15B are connected to IMD 16 using electrical leads 13, and may be affixed to an external surface of the stomach via sutures, surgical adhesives or the like. IMD 16 provides electrical stimulation of the stomach 12 through stimulation electrodes 15 to induce symptoms of nausea, satiety, bloating or gastric discomfort as part of treatment for obesity. Based upon experimental work associated with gastric stimulation for gastroparesis, these symptoms associated with gastroparesis may be induced using a stimulation signal described in more detail in regard to FIG. 3. More significantly, IMD 16 may induce these symptoms as a mechanism to discourage consumption of food without disrupting normal stomach motility associated with gastroparesis. The undesirable symptoms serve as negative biofeedback, discouraging the patient from consuming additional food, but permit continued stomach motility. As such, undesirable consequences of gastroparesis may be avoided, such as reduced ability to receive nutrition. In addition, in some embodiments, electrical stimulation can be selectively applied at particular times so that the patient 10 need not subjected to continuous symptoms of gastroparesis.

For example, IMD 16 may provide electric stimulation to stimulation electrodes 15 to induce the desired symptoms during a time period in which IMD 16 is instructed to provide such stimulation. In various embodiments, gastric electric stimulation may be controlled by a patient. Using an external module 20, a patient may command IMD 16 to begin and then end gastric electric stimulation at times selected by the patient, such as meal times or snack times. In other embodiments, IMD 16 may automatically initiate gastric electric stimulation at predetermined periods of time during the day. These periods of time may correspond to immediately before and during expected meal times. The time for such time periods may be set and modified using external module 20 communicating with IMD 16, or by a physician responsible for programming the functionality of the IMD. Other embodiments may utilize any other time period selection mechanism to induce symptoms at times during the day in which a patient may be expected to consume food.

In all of these embodiments, obesity patients experience uncomfortable symptoms during time periods associated with eating and may alter their behavior to eat less food. In addition, IMD 16 may alter the length of time during which electric stimulation is provided to discourage consumption of larger portions of food. Upon receipt of commands from external module 20, according to some embodiments, IMD 16 may provide additional electric stimulation in order to induce symptoms for a longer period of time to further discourage consumption of food. Yet, patient 10 need not experience the symptoms continuously and, importantly, can benefit from the symptoms without actually experiencing significant gastroparesis.

The length of time electric stimulation is needed to adequately control excess consumption of food, and thus treat obesity, may vary from patient to patient. For some patients, providing electric stimulation during meal times may be sufficient to effectively treat obesity. In other patients, electric stimulation may be needed at various times throughout a day in order to discourage snacking and related consumption of food at times other than regularly scheduled meals to provide an effective treatment for obesity. IMD 16 may be configured to provide gastric electric stimulation to induce symptoms at these various times during a day, either automatically according to stored times, or manually in response to command entered by the user via external module 20. An external module 20 may be desirable as patient 10 may wish to alter occurrence of these periods of electric stimulation during a particular time period of treatment for obesity without necessarily returning to a physician for reprogramming of IMD 16.

In some embodiments, IMD 16 may communicate with patient 10 via external module 20 to receive commands as discussed above. External module 20 may be a device dedicated to receiving user input pertaining to electric stimulation and transmitting corresponding commands to IMD 16. In some cases, external module 20 may present status information indicating operational status of IMD 16, as well as elapsed or remaining time for a current electrical stimulation period. Also, external module 20 may receive and present information concerning sensed physiological parameters, as will be described below. External module 20 may also be a general purpose device such as a pager, cellular telephone, or personal digital assistant (PDA). As shown in FIG. 1, IMD 16 communicates wirelessly with external module 20 via radio frequency (RF) telemetry, but the communication may also be transmitted via a wired connection, an optical connection, or a transcutaneous communication link.

In addition, in some embodiments, IMD 16 may measure a characteristic of one or more physiological parameter using various sensors (not shown) connected to IMD 16. These physiological parameters may be used in determining when gastric electric stimulation may be applied to the gastrointestinal tract of patient 10. For example, IMD 16 may be responsive to sensed physiological parameters to automatically deliver electrical stimulation. Alternatively, IMD 16 may communicate the parameters, states indicated by the parameters, or operational status, to patient 10, e.g., via visible or audible output media provided by external module 20, such as lights, LEDs, a display or an audio speaker. An audio message may take the form of an audible beep, ring, speech message or the like. Additional details regarding use of physiological parameters in providing gastric electric stimulation, is described in commonly assigned and co-pending U.S. patent application to Starkebaum, entitled "GASTRIC STIMULATION RESPONSIVE TO SENSED FEEDBACK," Ser. No. 60/265,497, filed Jan. 31, 2001. This related application is incorporated by reference herein in its entirety.

IMD 16 may consist of a pair of stimulation electrodes 15. The stimulation electrodes 15 may consist of intramuscular electrodes or surface electrodes. Intramuscular electrodes are placed in the muscle wall of the stomach, preferably in the circular muscle layer. These stimulation electrodes may be inserted either from the serosal aspect of the stomach (i.e., the from the outer surface) or from the musosal aspect (i.e., from the inside side of the stomach. Surface electrodes may be attached to the serosa or mucosa, though the serosa is preferred.

Stimulation electrodes 15, such as the model 4351 stimulation electrodes and leads manufactured by Medtronic, Inc., and are connected to IMD 16. IMD 16 may be an implanted stimulator, such as model 7425 or model 3116 implantable stimulator manufactured by Medtronic, Inc.

Figure 1B:
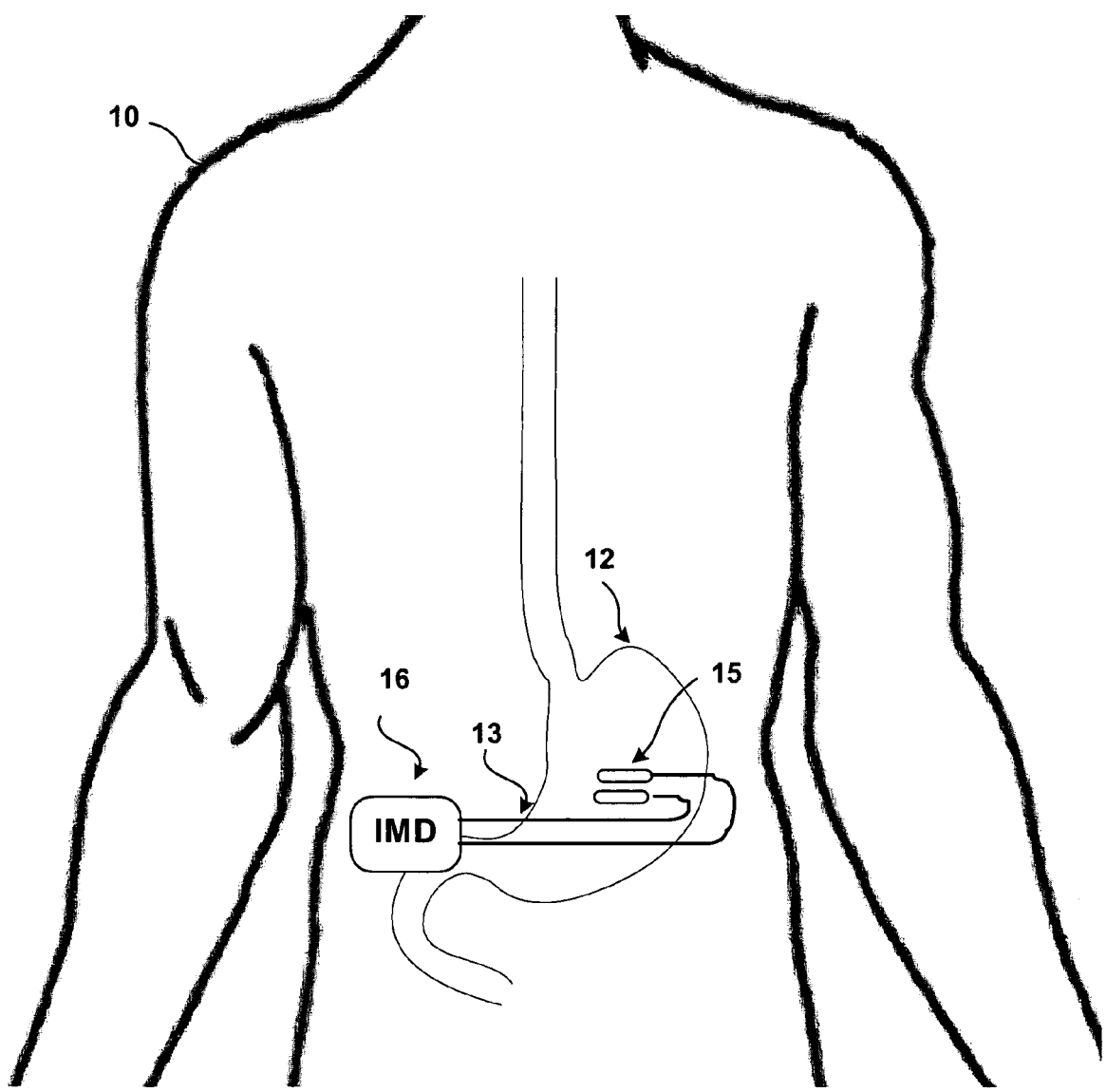

The pair of stimulation electrodes 15 may be placed in the muscle wall of the stomach using standard surgical practices including laparotomy or laparoscopy, as shown in FIG. 1B. The pair of stimulation electrodes 15 may be positioned anywhere in the stomach, but typically are placed along either the greater curvature or lesser curvature. IMD 16 may be positioned subcutaneously in the abdominal wall, typically in the right mid quadrant and may then be programmed by radio-telemetry link to the appropriate stimulation parameters using an external module 20. FIG. 1B illustrates a pair of stimulation electrodes 15 positioned along greater curvature. In other embodiments, stimulation electrodes capable of being positioned either on the stomach wall or embedded within the muscle wall may be used without departing from the spirit and scope of the present invention. Attachment of the stimulation electrodes 15 may be accomplished by means of sutures, surgical clips, or screws, such as are typically used with screw-in leads.

The foregoing describes the operation of IMD 16 in an embodiment of the present invention operating in an open loop mode. An open loop system may subject the patient to unpleasant GI symptoms longer than necessary each day to discourage decreased food intake and weight loss. Additionally, continuous operation of the stimulator may result in unacceptable power consumption and a resulting short battery life. Operation of IMD 16 in an embodiment of the present invention that uses a closed loop mode may overcome these shortcomings.

It is known that symptoms such as nausea are associated with certain physiological parameters that may be sensed to control the operation of IMD 16. In alternate embodiments of IMD 16, these physiological parameters may be sensed and then used to control generation of the electric stimulation signal.

In one case, it has been shown that tachygastria, i.e., an abnormally fast gastric slow wave, is associated with nausea. See Koch et al., page 198, Chapter 13, Electrogastrography, in Gastrointestinal Motility in Health and Disease, ed. Schuster, Crowell, Koch; B C Deckere, $2^{nd}$ Edition, 2002. Thus, the appearance of tachygastria sensed from electrodes in the stomach may be used to control IMD 16.

Various prior gastric stimulation systems monitor an electrical signal from the stomach and then use this sensed electrical signal to control a gastric stimulation system for the purpose of treating gastric arrhythmias and functional gastrointestinal disorders. See commonly assigned U.S. patents to Bourgeois et al described above for examples of these gastric stimulation systems. Sensing techniques similar to those described by Bourgeois may be used to control a gastric stimulator for the purpose of modulating gastrointestinal symptoms for treatment of obesity. A patient's gastrointestinal tract may be electrically stimulated using IMD 16. IMD 16 may also sense a gastric slow wave as described in Bourgeois et al. If an abnormal slow wave is not detected, IMD 16 may continue to operate as described above in open loop embodiments of IMD 16.

If the sensed slow wave is abnormal in that the sensed slow wave is either too slow or too fast, a timer within IMD 16 may be set to turn the stimulator OFF after a predetermined time. Alternatively, a timer may be set to modify various electric stimulation signal parameters. For example, either the stimulator amplitude or pulse width may be modified after a predetermined time to reduce the intensity of the induced nausea. The predetermined time may vary between 0 and 24 hours, although the preferred time interval is between 0 and 6 hours. In humans, the normal gastric slow wave frequency is 3 cycles per minute. As such, a gastric slow wave may be considered abnormally slow when the sensed gastric slow wave is less than 2.5 cycles per minute. Similarly, a slow wave may be considered abnormally fast when the sensed gastric slow wave is greater than 3.5 cycles per minute.

Additionally, it has been shown that contractile activities in the duodenum and small intestine occur during nausea. See Lacy et al, page 1478, Chapter 10, Manometry, in Gastrointestinal Motility in Health and Disease, ed. Schuster, Crowell, Koch; B C Deckere, $2^{nd}$ Edition, 2002. Therefore, peristaltic contractions from the duodenum, small intestine, or other regions of the gastrointestinal tract may be measured using strain gauges or other means, and such contractions may be used instead of a gastric slow wave to control generation of an electric stimulation signal by IMD 16 after a predetermined period of time as described above. Other similar physiological parameters may be utilized without departing from the spirit and scope of the present invention.

Figure 2A:
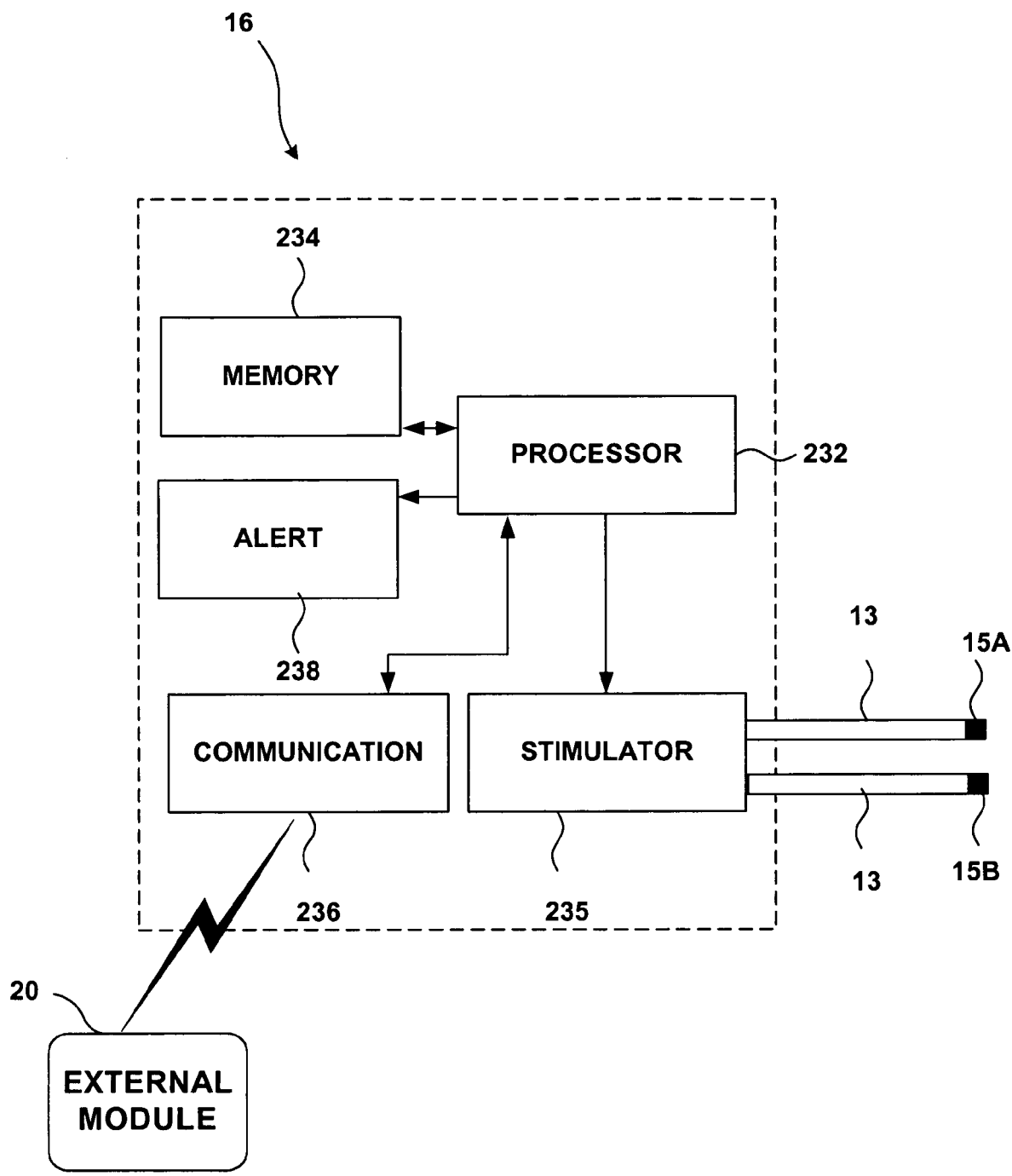
FIGS. 2A and 2B is a block diagram illustrating constituent components of an embodiment of the invention depicted in FIG. 1A.
Figure 2B:
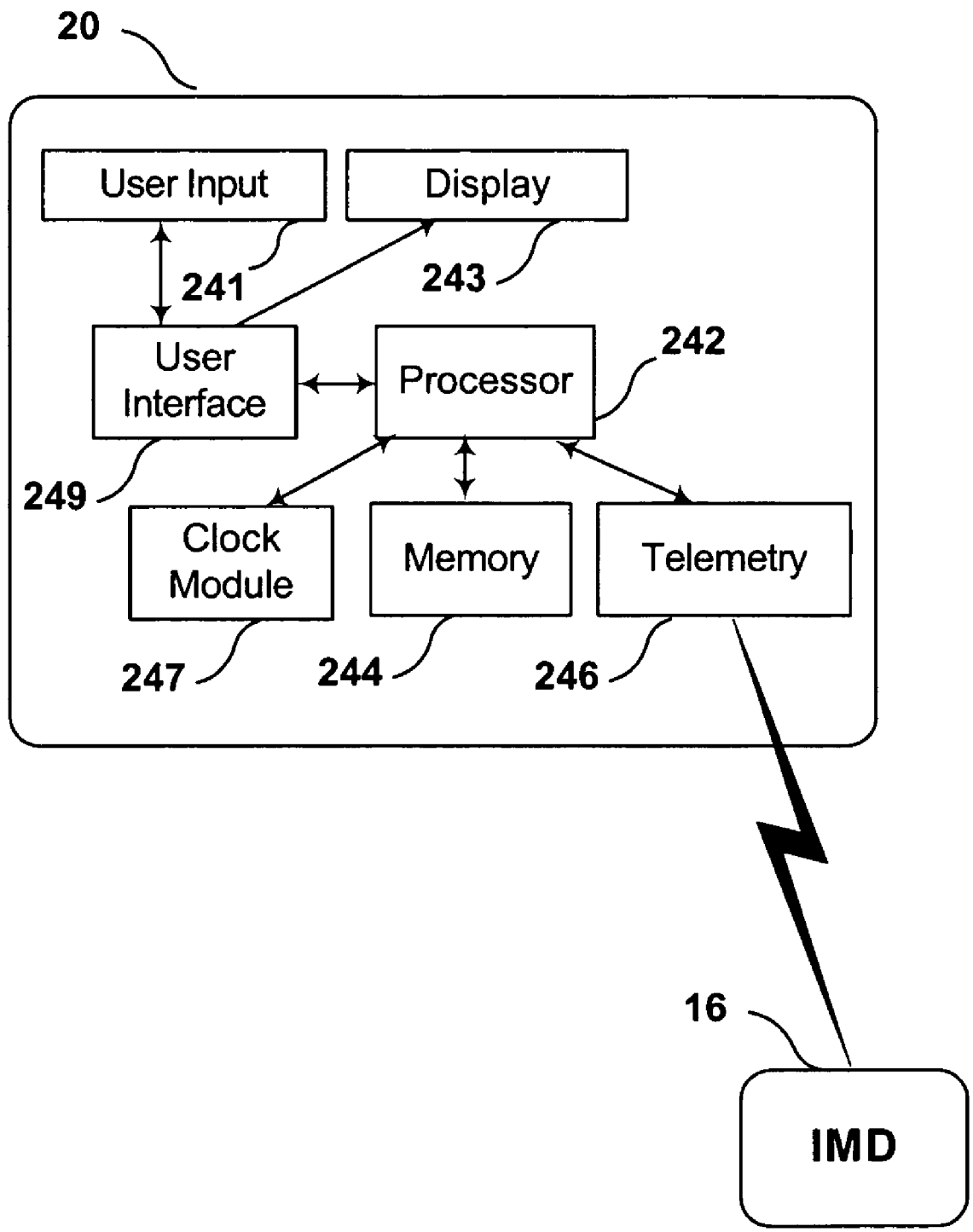

FIGS. 2A and 2B are block diagrams illustrating an embodiment of the invention. In FIG. 2A, IMD 16 receives external commands from external module 20 and stores the commands within memory 234. Memory 234 may include any form or volatile memory, non-volatile memory, or both. In one embodiment, the external command consists of a command operation field and a command time of day field. The command operation field is used to indicate whether electrical stimulation is to be initiated or whether electrical stimulation is to be terminated. The command time of day field is used to indicate the time of day when the command operation is to occur.

In addition to received external commands, memory 234 may store records concerning measurements of detected physiological parameters, applicable thresholds, communications to patient 10 or other information pertaining to operation of IMD 16. Memory 234 may also store information about patient 10. In addition, processor 232 is typically programmable, and programmed instructions reside in memory 234.

Processor 232 determines whether to direct delivery of a electric stimulation signal via stimulator 235 and stimulation electrodes 15 for transmission to patient 10 at a current time of day maintained within processor 232. As shown below, processor 232 may compare the current time of day obtained from an on-board clock (not shown) within IMD 16 or a clock signal received with external commands from external module 20 to one or more programmed times, stored within memory 234, for delivery of electrical stimulation, and may automatically generate an electric stimulation signal using stimulator 235. Alternatively, the current time of day may be compared to start and end times communicated by the command time of day field in an external command received from external module 20. The start and end times may be specified explicitly, e.g., 11:45 am and 12:15 pm, or by specifying a duration, e.g., twenty minutes. As a further alternative, processor 232 may simply be responsive to start and stop commands from external module 20.

Stimulator 235 may comprise suitable circuitry for generating an electrical stimulation signal with desired amplitude, frequency, pulse width and duration to induce symptoms of gastroparesis without substantially disrupting normal stomach motility. This electric stimulation signal is applied to a patient's gastrointestinal tract. Again, this electric stimulation signal may be generated until processor 232 receives an external command instructing an end to electric stimulation, or until the current time of day corresponds to a stored end time or a time indicated by a received external command indicating that electric stimulation is to end. Processor 232 may also record the occurrence of electric stimulation within memory 234 for later use. Notably, the electrical stimulation signal need not be delivered continuously, but rather may be targeted to coincide with meal or snack times. Also, in some embodiments, the severity symptoms may be sufficient to discourage overeating, but still permit the patient to consume a prescribed amount of food.

When processor 232 generates the electric stimulation signal, processor 232 may also convey the communication to patient 10 by a number of channels. IMD 16 may include, for example, a communication module 236 to wirelessly transmit the communication to external module 20. In addition to transmitting a communication to an external module 20, communication module 236 may be configured to wirelessly transmit information about the history or status of IMD 16 to the physician for patient 10.

In addition or in the alternative, IMD 16 may include an alert module 238 that is implanted in the body of patient 10. When activated by processor 232, alert module 238 can notify patient 10 directly without an external module. Alert module 238 may, for example, notify patient 10 audibly or by vibration. For example, alert module 238 may take the form of a piezoelectric transducer that is energized in response to a signal from processor 232 in order to emit a sound or vibration. In each case, patient 10 receives a communication that IMD 16 is delivering electrical stimulation to the gastric tract, and can thereby be better prepared to experience symptoms of gastroparesis, which may be imminent.

In FIG. 2B, external module 20 generates external commands for transmission to IMD 16 via telemetry module 246. External module 20 consists of processor 242, user interface module 249, clock module 247, memory 244, telemetry module 246, user inputs 241, and display 243. In FIG. 2B, external module 20 receives user commands from user inputs 241 and stores the commands within memory 244. Memory 244 may include any form or volatile memory, non-volatile memory, or both. In one embodiment, the user command consists of an input signal from a user input device such as depressible button. The input signal is received within user interface module 249 and is used in generation of external commands.

Memory 244 may also store records concerning measurements of detected physiological parameters, applicable thresholds, communications to patient 10 or other information pertaining to operation of IMD 16. Memory 244 may also store information about patient 10. In addition, processor 242 is typically programmable, and programmed instructions reside in memory 244.

User interface module 249 interacts with display 243 to present data generated by processor 242 to patient 10. Display 243 consists of a display device capable of displaying a user interface image to patient 10. The display device may be an LCD screen capable of rendering a computer generated image in either color or grayscale. Other types of display devices such as LED-based display devices, video tube based display devices and similar display devices capable of rendering a computer generated image may be used. In one embodiment, external device is a handheld device capable of being carried or worn by patient 10. In other embodiments, external module 20 is an interface device attached to a personal computer executing a program to generate a user interface display within a window on the display device of the personal computer.

Display 243 and user inputs 241 work together with user interface module 249 to provide a user interface mechanism allowing patient 10 to enter user commands into external module 20 for use in generating external commands controlling the operation of IMD 16. Display 243 and user inputs 241 also work together with user interface module 249 to provide a user interface mechanism allowing patient 10 receive data from IMD 16 useful to patient 10.

Processor 242 receives user commands from interface module 249 and processes them to generate external commands for IMD 16. The external commands may be transmitted to IMD 16 through telemetry module 246. Processor 242 is coupled to clock module 247 to obtain time of day data for use in generating external commands. Clock module 247 maintains a running clock to provide processor 242 with current time of day information.

Telemetry module 246 communicates with communications module 236 within IMD 16 to provide a communications channel between IMD 16 and external module 20. External commands pass through this communications channel from external module 20 to IMD 16. Patient data sensed by IMD 16 passes through the communications channel from IMD 16 to external module 20.

Figure 3:
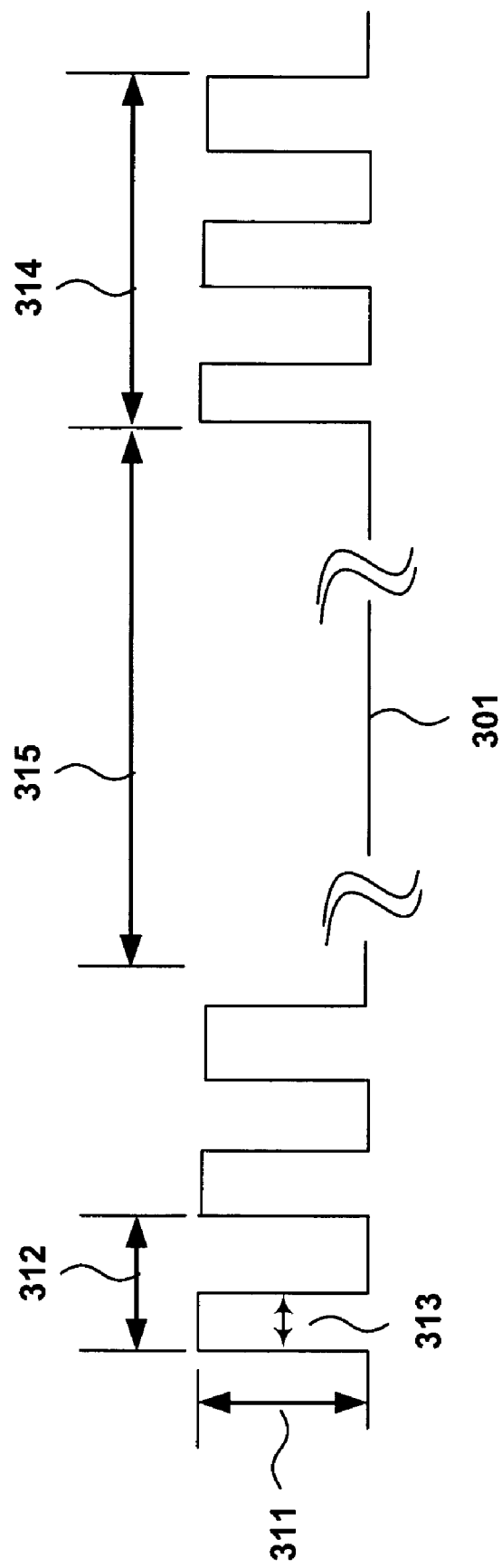
FIG. 3 is a diagram illustrating an exemplary electric stimulation signal applied to a patient's gastrointestinal tract to induce symptoms of gastroparesis.

FIG. 3 is a diagram illustrating an exemplary electric stimulation signal 301 applied to a patient's gastrointestinal tract to induce symptoms of gastroparesis. Based upon experimental work associated with gastric stimulation of gastroparesis, an electrical stimulation signal 301 is believed to induce symptoms of gastroparesis by activating an afferent pathway to patient 10 brain the via the patient's vagal nerve. In accordance with the invention, this electrical stimulation using electric stimulation signal of FIG. 3 typically does not cause substantial disruption in the normal stomach motility, thereby reducing adverse health effects for patient 10.

Electric stimulation signal 301 possesses a set of signal parameters including amplitude 311, signal frequency 312, pulse width 313, and a duty cycle with an on period 314 and an off period. Experimentally, preferred values for these set of signal parameters are amplitude 311=5 mA, signal frequency 312=14 Hz, pulse width=330 microseconds, and a duty cycle with on period 314=0.1 seconds and an off period=5 seconds. The signal parameters above, and particularly frequency 312, are significantly higher than the normal gastric slow wave of a typical human stomach, and utilize shorter pulse widths than is typically used to disrupt normal stomach motility. Consequently, substantial disruption of stomach motility can be avoided. At the same time, however, patient 10 nevertheless experiences symptoms, i.e., sensations, of gastroparesis, such as nausea, satiety, bloating or discomfort. The amplitude 311 above is specified as a signal current value expressed in milliamperes. One skilled in the are will recognize that the amplitude 311 may also be expressed as a corresponding voltage value given an impedance value corresponding to a circuit from IMD 16 through electrical leads 13, stimulation leads 15 and stomach tissue. In many embodiments, this impedance value is approximately 500 Ohms.

Some representative or exemplary ranges of preferred electrical pulse stimulation parameters capable of being delivered by IMD 16 through stimulator 235 and stimulation electrodes 15 without disrupting stomach motility are set forth as follows. A suitable frequency is in the range of approximately 0.5 Hz to 500 Hz, preferably 10 Hz to 250 Hz, and more preferably 14 Hz to 100 Hz. A suitable pulse width is in the range of approximately 10 microseconds to 5000 microseconds, preferably 100 to 1000 microseconds, and more preferably 180 to 450 microseconds. A suitable duty cycle has an on period in the range of approximately 0.1 seconds to 1 second, preferably 0.1 to 0.5 seconds, and more preferably 0.1 to 0.25 seconds. A suitable duty cycle also has an off period in the range of approximately 1 second to 60 seconds, preferably 1 to 10 seconds, and more preferably 1 to 5 seconds. Delivery of an electrical stimulation signal having parameters as described above may be effective in inducing symptoms of gastroparesis without substantially disrupting stomach motility.

Figure 4:
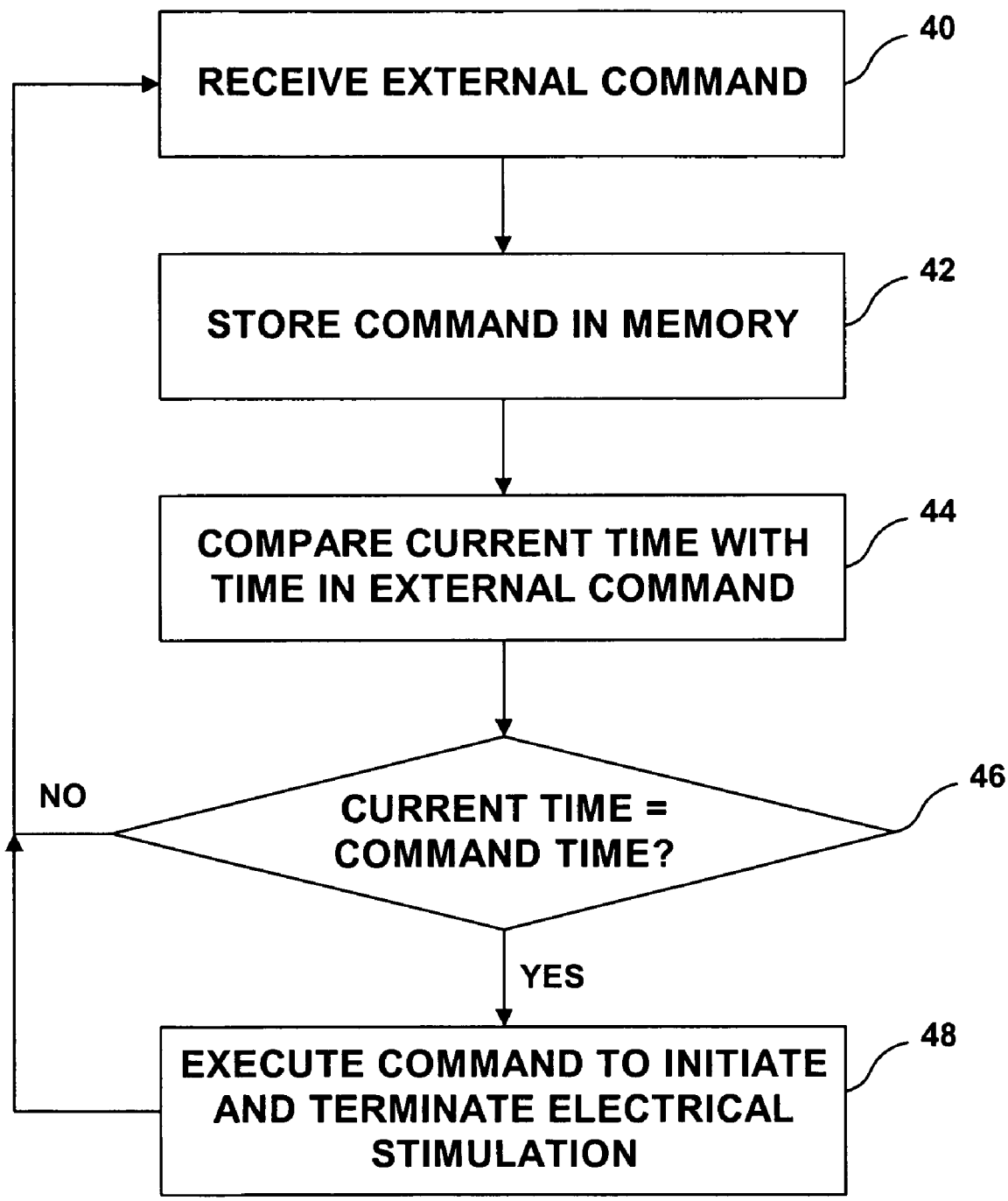
FIG. 4 is a flow diagram illustrating a technique for providing gastric electric stimulation.

FIG. 4 is a flow diagram illustrating a technique for providing gastric electric stimulation. Processor 232 receives an external command regarding initiating and terminating electric stimulation from external module 20 (40). These external commands indicate when to initiate electric stimulation and when to terminate electric stimulation. The external commands may specify that the electric stimulation is to be initiated and/or be terminated immediately, or may specify a time of day when the electric stimulation is to start and end. The external commands may also specify a set of signal parameters used to generate an electric stimulation signal used when generating electrical stimulation to induce symptoms of gastroparesis without disruption of normal stomach motility.

Processor 232 processes the external command received from external module 20 and stores the external command into memory 234 (42). The external commands, when stored within memory 234, are used to indicate when electric stimulation is to occur if the external command does not instruct IMD 16 to immediately initiate and terminate electric stimulation. Processor 232 maintains a current time of day value using an internal clock for use with the stored external commands.

During normal operation processor 232 compares the current time of day from its internal clock with the external commands stored within memory 234 (44) in order to determine if current electric stimulation activity is to be altered. When the current time of day equals a time of day contained within a stored external command, processor 232 performs an operation contained within the stored external command. This command may instruct processor 232 to generates a electric stimulation signal, using stimulator 235, in order to induce gastroparesis symptoms to patient 10 (48). Alternately, this command may instruct processor 232 to terminate generation of a electric stimulation signal, using stimulator 235 (48). When the current time of day equals a time of day contained within any stored external command, processor 232 may continue to receive and process external commands transmitted by external monitor, as well as continually compare the current time of day with stored external commands as time passes. In some implementations, a current time of day will "equal" a time of day contained within a stored external command when the time of day values are identical, and in other implementations, a current time of day will "equal" a time of day contained within a stored external command when the current time of day is earlier than the time of day contained within a stored external command.

Figure 5:
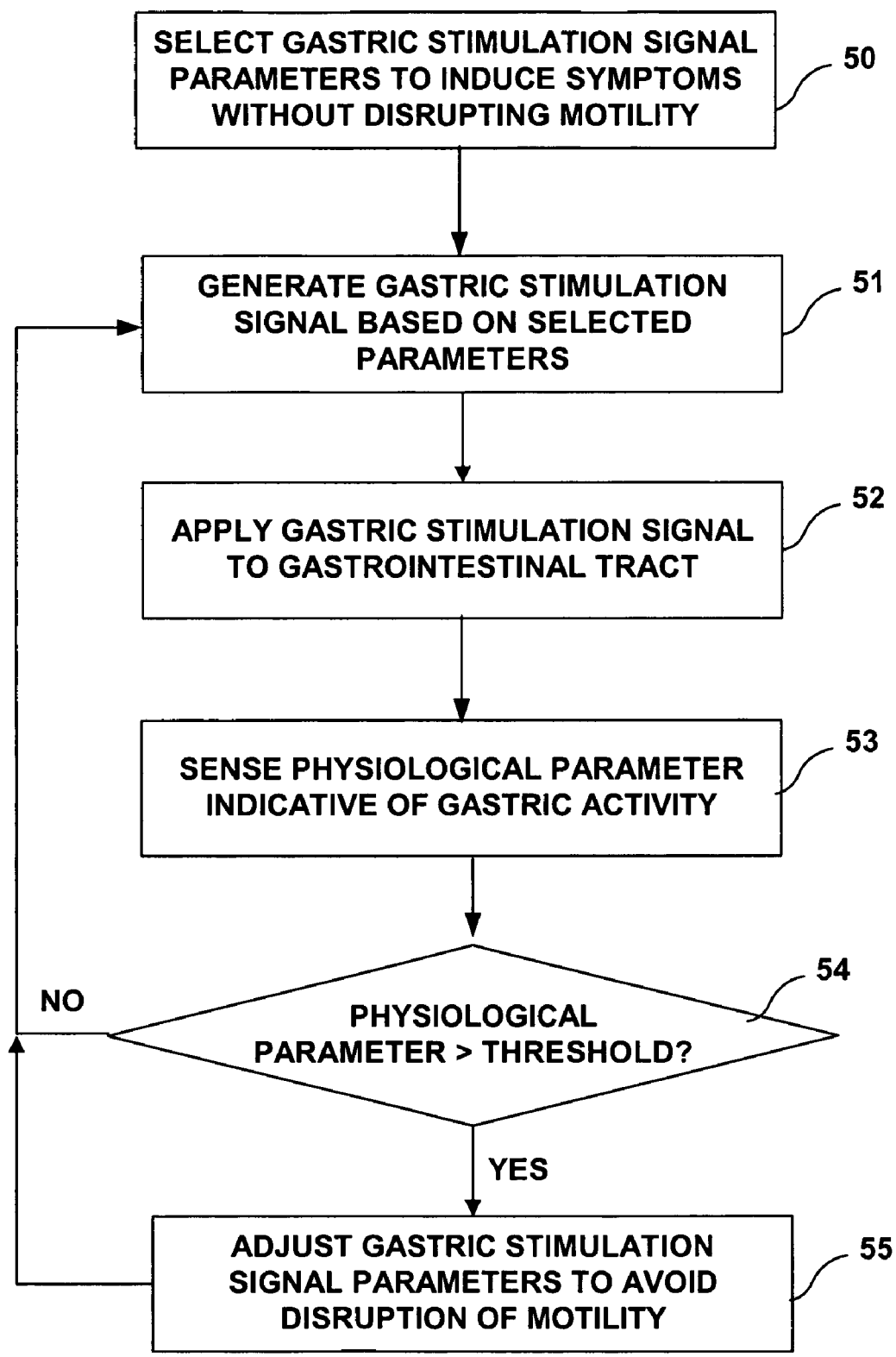
FIG. 5 is a flow diagram illustrating a technique for utilizing gastric electric stimulation.

FIG. 5 is a flow diagram illustrating a technique for utilizing gastric electric stimulation. Processor 232 controls the generation of an electric stimulation signal, using stimulator 235, in order to induce gastroparesis symptoms to patient 10. Processor 232 controls the generation of the electric stimulation signal by selecting a set of signal parameters utilized in inducing desired symptoms without substantially reducing normal stomach motility (50). The electric stimulation signal possesses the electrical signal parameters as described herein in order to induce desired symptoms without reducing normal stomach motility. Once the electric stimulation signal is properly defined in terms of the set of signal parameters, processor 232 controls an appropriate time to generate and transmit the electric stimulation signal for providing treatment to a patient for obesity (51).

Processor 232 also controls transmission of the electric stimulation signal from stimulator 235 to patient 10. Processor 232 commands stimulator 235 to transmit the electric stimulation signal (52) to patient 10 to induce the desired symptoms without reducing normal stomach motility. Processor 232 also commands stimulator 235 to terminate transmission of the electric stimulation signal in response to external commands received from external module 20 as discussed above.

In some embodiments, processor 232 may sense a physiological parameter (53) in order to determine whether electrical stimulation signal parameters are appropriately selected to induce desired symptoms without substantially reducing normal gastric motility. Processor 232 may compare the sensed physiological parameters with a predetermined threshold (54) in order to determine whether electric simulation signal parameters require modification. If the level of the sensed physiological parameters does not satisfy an applicable predetermined threshold, i.e., is greater than or less than the threshold, the electrical signal parameters of the stimulation signal may be modified (54). Failure to satisfy the threshold may provide an indication that the stimulation signal is causing undesirable disruption of stomach motility.

The physiological parameter may be any of a variety of parameters such as an electrical signal level, frequency, duty cycle, or the like, which is indicative of stomach motility. Alternatively, the morphology of a physiological waveform may be analyzed and compared to reference points or a signal waveform template to indicate stomach motility. In either case, if stomach motility is significantly compromised, modifications to the stimulation signal may include increasing or reducing signal amplitude, signal pulse width, signal frequency, and signal duty cycle, so that symptoms of gastroparesis are still induced, yet stomach motility remains substantially normal. Alternatively, modifications may include termination of transmission of the electrical stimulation signal completely if abnormal stomach motility is detected from the sensed physiological parameter. In any case, transmission of the electric stimulation signal may be initiated and terminated using any mechanism for controlling the electric stimulation signal including time of day control, manual patient control, and sensed physiological parameters for closed loop control as discussed above without departing from the spirit and scope of the present invention.

The invention further encompasses one or more computer-readable media comprising instructions that cause a processor, such as processor 232 and processor 242, to carry out the techniques of the invention. A computer-readable medium includes, but is not limited to, any magnetic or optical storage medium, ROM or EEPROM.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems as described herein. Furthermore, the invention includes embodiments that use techniques to sense physiological parameters in addition to those specifically described herein.

Moreover, the invention includes embodiments in which IMD 16 is not be dedicated to sensing stomach activity and providing gastric stimulation, but performs other functions as well. IMD 16 may include, for example, an implantable drug delivery system such as any of a number of SynchroMed pumps manufactured by and commercially available from Medtronic Inc. In such embodiments, IMD 16 may actively administer therapy, such as by dispensing insulin or medication, in addition to generating a communication to patient 10.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A method for providing gastric stimulation to induce symptoms in a patient, the method comprising:
   generating an electric stimulation signal for inducing symptoms in the patient; and applying the electric stimulation signal to a gastrointestinal tract of the patient;
wherein the electric stimulation signal induces symptoms of gastroparesis in the patient without substantially disrupting stomach motility.

2. The method according to claim 1, wherein the electric stimulation signal has a frequency significantly greater than a normal gastric slow wave of the patient.

3. The method according to claim 1, wherein the symptoms include at least one of nausea, satiety, and gastric discomfort.

4. The method according to claim 1, further comprising:
receiving an external command for initiating and terminating electric stimulation; and
generating the electric stimulation signal in response to the external command.

5. The method according to claim 4, wherein the external command comprises:
a command operation; and
a command time of day when the command operation is to occur.

6. The method according to claim 4, wherein the external command indicates initiation of the application of the electric stimulation signal.

7. The method according to claim 4, wherein the external command indicates termination of the application of the electric stimulation signal.

8. The method according to claim 1, wherein the electric stimulation signal comprises a set of signal parameters comprising an amplitude, a signal frequency, a pulse width, and a duty cycle, and at least one of the parameters is selected to be insufficient to cause disruption of normal stomach motility.

9. The method according to claim 1, wherein the electric stimulation signal comprises a set of signal parameters, the set of signal parameters comprising:
an amplitude between approximately 1 mA and 100 mA;
a signal frequency between approximately 0.5 Hz and 500 Hz;
a pulse width between approximately 10 microseconds and 5000 microseconds;
an on duty cycle between approximately 0.1 seconds and 1 second; and
an off duty cycle between approximately 1 second and 60 seconds.

10. The method according to claim 1, wherein the electric stimulation signal comprises a set of signal parameter, the set of signal parameters comprising:
an amplitude between approximately 0.1 mA and 10 mA;
a signal frequency between approximately 10 Hz and 250 Hz;
a pulse width between approximately 100 microseconds and 1000 microseconds;
an on duty cycle between approximately 0.1 seconds and 0.5 seconds; and
an off duty cycle between approximately 1 second and 10 seconds.

11. The method according to claim 1, wherein the electric stimulation signal comprises a set of signal parameter, the set of signal parameters comprising:
an amplitude of approximately 5 mA;
a signal frequency of approximately 14 Hz;
a pulse width of approximately 330 microseconds;
an on duty cycle of approximately 0.1 seconds; and
an off duty cycle of approximately 5 seconds.

12. The method according to claim 1, wherein the method further comprises:
sensing a physiological parameter associated with the gastrointestinal tract; and
adjusting the set of signal parameters based upon the sensed physiological parameter.

13. The method according to claim 12, wherein adjusting the set of signal parameters results in termination of generation of the electric stimulation signal.

* * * * *